United States Patent
Garbini et al.

(10) Patent No.: US 9,261,595 B2
(45) Date of Patent: Feb. 16, 2016

(54) ACOUSTIC ARRAY WITH A SHAPE ALLOY FOR MEDICAL ULTRASOUND

(75) Inventors: Lex J. Garbini, El Granada, CA (US); Walter T. Wilser, Cupertino, CA (US); Stephen R. Barnes, Bellevue, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2303 days.

(21) Appl. No.: 11/903,287

(22) Filed: Sep. 21, 2007

(65) Prior Publication Data
US 2008/0125661 A1    May 29, 2008

Related U.S. Application Data

(63) Continuation-in-part of application No. 11/605,738, filed on Nov. 28, 2006, now Pat. No. 8,449,467.

(51) Int. Cl.
| | | |
|---|---|---|
| G01S 15/89 | (2006.01) | |
| A61B 8/08 | (2006.01) | |
| B06B 1/06 | (2006.01) | |
| G01S 7/52 | (2006.01) | |
| A61B 8/00 | (2006.01) | |
| A61B 8/12 | (2006.01) | |

(52) U.S. Cl.
CPC ............ *G01S 15/8929* (2013.01); *A61B 8/445* (2013.01); *A61B 8/483* (2013.01); *B06B 1/0622* (2013.01); *G01S 7/52079* (2013.01); *A61B 8/12* (2013.01); *A61B 8/4488* (2013.01); *G01S 15/8993* (2013.01); *Y10T 29/49908* (2015.01)

(58) Field of Classification Search
CPC .................................................. B06B 1/0622
USPC .............. 600/437, 459; 73/584, 587, 645; 310/311, 322; 367/61, 62, 72, 117, 367/138, 140, 153–167
See application file for complete search history.

(56) References Cited

U.S. PATENT DOCUMENTS

| | | |
|---|---|---|
| 4,202,050 A | 5/1980 | Klein |
| 4,515,017 A | 5/1985 | McConaghy |
| 4,567,895 A | 2/1986 | Putzke |
| 5,199,437 A | 4/1993 | Langberg |
| 5,291,893 A | 3/1994 | Slayton |
| 5,388,584 A | 2/1995 | King |

(Continued)

FOREIGN PATENT DOCUMENTS

WO    WO 2006119173    11/2006

OTHER PUBLICATIONS

Turnbull, DH et al., "Beam Steering with Pulsed Two-Dimensional Transducer Arrays", IEEE Transactions on Ultrasonics, Ferroelectrics and Frequency Control, vol. 38, No. 4, Jul. 1991.

(Continued)

*Primary Examiner* — Unsu Jung
*Assistant Examiner* — Daniel Huntley (57) ABSTRACT

A memory alloy is used during manufacture of a transducer. The memory of the alloy may correct for deviations or bending during manufacture, such as a superelastic alloy returning an array to a flat state after being twisted during handling. The memory of the alloy may cause a desired change in array geometry during manufacture, such as a shape memory alloy twisting an array into a curved or helix due to applied heat. The array may be fixed in place by the memory alloy or bonding after positioning by the memory alloy, preventing further substantial alteration.

12 Claims, 3 Drawing Sheets

(56) References Cited

U.S. PATENT DOCUMENTS

| | | | |
|---|---|---|---|
| 5,397,301 | A | 3/1995 | Pflueger et al. |
| 5,505,205 | A | 4/1996 | Solomon et al. |
| 5,546,946 | A | 8/1996 | Souquet |
| 5,680,863 | A | 10/1997 | Hossack et al. |
| 5,735,282 | A | 4/1998 | Hossack |
| 5,876,345 | A | 3/1999 | Eaton et al. |
| 5,916,168 | A | 6/1999 | Pedersen et al. |
| 6,059,731 | A | 5/2000 | Seward et al. |
| 6,126,602 | A | 10/2000 | Savord et al. |
| 6,155,979 | A | 12/2000 | Moser |
| 6,159,153 | A | 12/2000 | Dubberstein et al. |
| 6,447,478 | B1 * | 9/2002 | Maynard ............ 604/95.05 |
| 6,592,520 | B1 | 7/2003 | Peszynski et al. |
| 6,676,602 | B1 | 1/2004 | Barnes et al. |
| 6,709,396 | B2 | 3/2004 | Flesch et al. |
| 6,795,374 | B2 | 9/2004 | Barnes et al. |
| 6,969,354 | B1 | 11/2005 | Marian |
| 7,497,828 | B1 | 3/2009 | Wilk et al. |
| 2004/0111101 | A1 | 6/2004 | Chin |
| 2004/0158153 | A1 | 8/2004 | Hirt et al. |
| 2006/0173348 | A1 | 8/2006 | Wilser et al. |
| 2007/0038111 | A1 * | 2/2007 | Rehrig et al. ............ 600/459 |
| 2007/0066902 | A1 | 3/2007 | Wilser et al. |
| 2008/0125659 | A1 | 5/2008 | Wilser et al. |
| 2008/0287810 | A1 * | 11/2008 | Park et al. ............ 600/478 |
| 2009/0010459 | A1 | 1/2009 | Garbini et al. |

OTHER PUBLICATIONS

U.S. Appl. No. 11/605,738, filed Nov. 28, 2006.

PCT International Search Report, mailed Apr. 22, 2008, 6 pages total.

Bom, et al., *Early and recent intraluminal ultrasound devices,* International Journal of Cardiac Imaging, 1989, pp. 79-88, Kluwer Academic Publishers, Netherlands.

Seward, et al., *Transvascular and Intracardiac Two-Dimensional Echocardiography,* Echocardiography: A Journal of CV Ultrasound & Allied Tech., 1990, vol. 7, No. 4, pp. 457-464.

Schluter, et al., *Transesophageal cross-sectional echocardiography with a phased array transducer system Technique and initial clinical results,* Br Heart F, 1982, vol. 48, pp. 67-72.

Crowley, et al., *Optimized ultrasound imaging catheters for use in the vascular system,* International Journal of Cardiac Imaging 4, 1989, pp. 145-151, Kluwer Academic Publishers, Netherlands.

Valdes-Cruz, et al., *Transvascular Intracardiac Applications of a Miniaturized Phased-Array Ultrasonic Endoscope: Initial Experience With Intracardiac Imaging in Piglets,* Circulation, Mar. 1991, vol. 83, No. 3, pp. 1023-1027.

Crowley, et al., *Ultrasound guided therapeutic catheters: recent developments and clinical results,* International Journal of Cardiac Imaging 6, 1991, pp. 145-156, Kluwer Academic Publishers, Netherlands.

* cited by examiner

ACOUSTIC ARRAY WITH A SHAPE ALLOY FOR MEDICAL ULTRASOUND

RELATED APPLICATION

The present patent document is a continuation-in-part of application Ser. No. 11/605,738, filed on Nov. 28, 2006, now U.S. Pat. No. 8,449,467 the disclosure of which is hereby incorporated by reference.

BACKGROUND

The present embodiments relate to acoustic arrays for medical ultrasound. Acoustic arrays are formed from semi-conductor or piezoelectric material. Piezoelectric materials include solid piezoelectric or composites. The materials transduce between acoustic and electrical energies.

The material is divided into elements, such as dicing a slab of piezoelectric material into a linear array of elements. By mounting on a rigid or semi-rigid backing, the array of elements maintains a desired planar emitting face. The arrangement of elements may be curved for a curved linear array. For example, an array formed from piezoelectric composite material is warped. The elements on the end are positioned away from an azimuth axis. The emitting face of the array is flat in elevation but curved along azimuth.

Acoustic arrays may be positioned in a catheter. Due to the size of the catheter, there may be limited space for conductors or mechanical structures. However, the ability to scan in three-dimensions from a catheter is desired, such as for ablation procedures. For example, U.S. Published Patent Application No. 2006/0173348 shows twisting a one-dimensional array in a catheter for volume imaging. As another example, U.S. Published Patent Application No. 2007/0066902 shows a multidimensional array that is hinged to expand for volume imaging. The hinge may use a memory metal for operation.

Other complex array geometries may be used. However, such arrays may require complex and expensive manufacturing techniques. Fixturing and components with machined parts that match the desired curvature may lead to high cost in materials, tooling, and labor.

BRIEF SUMMARY

By way of introduction, the preferred embodiments described below include methods, systems, improvements, and transducers. A memory alloy is used during manufacture of a transducer. The memory of the alloy may correct for deviations or bending during manufacture, such as a superelastic alloy returning an array to a flat state after being twisted during handling. The memory of the alloy may cause a desired change in array geometry during manufacture, such as a shape-memory alloy twisting an array into a curved or helix due to applied heat. The array may be fixed in place by the memory alloy or bonding after positioning by the memory alloy, preventing further substantial alteration.

In a first aspect, a method is provided for manufacturing an acoustic array. A plurality of ultrasound elements of the array connect with a memory alloy. A geometry of the array is altered with the memory alloy during manufacture of a transducer probe including the array.

In a second aspect, a transducer is provided for medical ultrasound. A plurality of elements defines an emitting face of an array. The elements are spaced at least along an azimuth axis. A memory alloy connects with the array. The memory alloy is stacked with the array along a range dimension where the range dimension is substantially orthogonal to the emitting face.

In a third aspect, a transducer is provided for medical ultrasound. A plurality of elements defines an emitting face of an array. The elements are spaced at least along an azimuth axis. A memory alloy connects with the array. The memory alloy is operable to establish, during manufacture, a fixed geometry of the array.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Shape-memory alloy or superelastic alloy components are used in ultrasound array fabrication. These alloys provide control over the final array geometry. The superelastic and shape-memory alloys are used to maintain any geometry or to create complex ultrasound array geometries using simple array fabrication techniques.

For example, a shape-memory alloy sheet is affixed to the back of an ultrasound array. The shape-memory alloy may have a helical or a curved shape stored in memory. During array fabrication, the shape-memory sheet is in a flat geometry. The flat geometry greatly simplifies the array manufacturing. During the plastic welding of the subsequent catheter manufacturing or other heat application, the shape-memory alloy reverts to the memorized helical or curved shape. The thermoplastic covering the array is soft enough that the array can assume the geometry defined by the shape-memory alloy. Use of the shape-memory alloy in this way allows the creation of complex array geometries while using the simple array manufacturing methods associated with building planar arrays.

As another example, a superelastic alloy maintains array flatness throughout processing. The superelastic alloy maintains the flatness of a planar array during the ultrasound catheter (or probe) fabrication processes. If the array is twisted, bent or otherwise deformed, the superelastic alloy returns the array to the flat position. The steady state geometry of the superelastic alloy may be non-flat, such as helical. The array and alloy are maintained flat during manufacture, but return to the other geometry of the superelastic alloy once released.

The array may be used in high-element count ultrasound catheters. For example, a helical array twists along an azimuth axis. Using a helical array with a large number of elements allows different scan planes to be scanned. By walking an aperture along the azimuth axis, the angles of the acoustic planes vary. A volume may be sampled. The helical geometry and use of such an array are disclosed in U.S. Published Application No. 20080125659 (Ser. No. 11/605,738, filed on Nov. 28, 2006), the disclosure of which is incorporated herein by reference.

Figure 1:
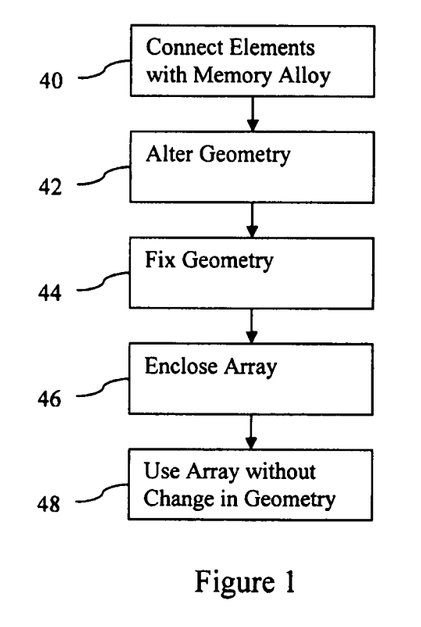
FIG. 1 is a flow chart diagram of one embodiment of a method for manufacturing and using an acoustic array.

FIG. 1 shows a method for manufacturing an acoustic array and scanning with the acoustic array. The method uses the system of FIG. 8, the array of FIGS. 2-3, or 5, or a different array and/or system. Additional, different, or fewer acts may be provided. For example, the geometry is not fixed in act 44, the array is not enclosed in act 46, and/or the array is not used in act 48.

In act 40, a plurality of ultrasound elements of the array are connected with a memory alloy. The connection may be a clamp or positioning in a fixture. In another embodiment, the elements connect to the memory alloy by bonding, such as with epoxy cured at room temperature or higher temperatures (e.g., 50 degrees Celsius). For example, a memory alloy is stacked with an array and other transducer layers used for an ultrasound transducer (e.g., a backing, a flex circuit with traces, a grounding plane, and/or matching layers). The stack is pressed and cured.

The memory alloy connects with the array directly or through one or more other components. For example, the memory alloy is stacked with an array of matching layer, transducer material, and backing block. Conductors, such as a flexible circuit extend from between the transducer material and the backing block. Excess flexible circuit material is positioned behind the backing block. The alloy is stacked directly against the backing block or the excess flexible circuit material is between the alloy and the array.

Figure 2:
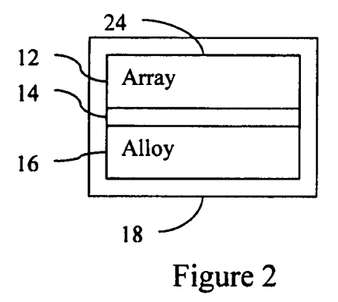
FIGS. 2-3 and 5 are cross-sectional views of different embodiments of a transducer array with memory alloy.

FIG. 2 shows one embodiment of a memory alloy 16 connected with an array 12 through one or more layers of conductors 14, such as an accordioned stack of flexible circuit material pressed together. The array 12 is a stack of transducer material and backing block with or without any matching layers and conductors. In other embodiments, the array 12 is only transducer material. The alloy 16 is below the array 12 and below the conductors 14. The conductors 14 are extend from the array 12 (e.g., between the transducer material and the backing) to behind the array 12. An enclosure 18 encloses the array 12 of elements 24. The layers are connected by bonding. The enclosure 18 connects with, rests against, or is spaced around the stack of the array 12.

Figure 3:
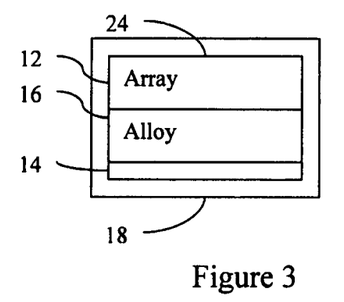

FIG. 3 shows an interconnected stack similar to FIG. 2, but with the memory alloy 16 between the array 12 of elements 24 and the conductors 14. Other arrangements may be used.

Figure 5:
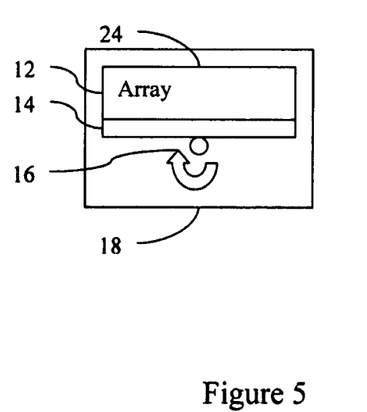

FIG. 5 shows the memory alloy 16 as a rod or tube rather than a sheet or plate of FIGS. 2 and 3. Other shapes and extents along any dimension may be used. In an alternative embodiment, the rod is flat on the side adjacent the array, but cylindrical on the bottom side (i.e., side away from the array 12). The cross-sectional area adjacent to the array 12 is maximized.

Figure 6:
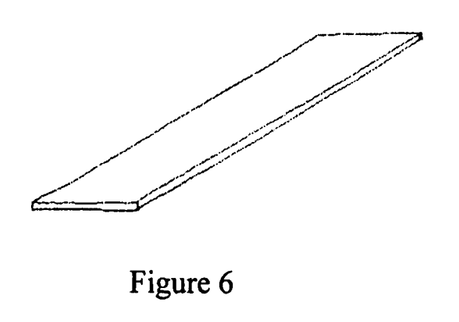
FIGS. 6 and 7 are graphical representations of one embodiment of a sheet of memory alloy in two different positions.

FIG. 6 shows the memory alloy 16 as a flat plate structure, such as associated with the memory alloy 16 shown in FIGS. 2 and 3.

In act 42 of FIG. 1, the geometry of the array is altered. The memory alloy alters the geometry during manufacture of a transducer probe including the array. The alloy alters the array to a desired geometry. Any geometry may be remembered by the memory alloy. For example, the desired geometry is flat or planar. As another example, the desired geometry is curved along one or more dimensions (e.g., curved along an azimuth dimension and not along an elevation dimension). In another embodiment, the desired geometry is a helical shape for the emitting face of the array.

The alteration occurs during manufacturing. For example, the alteration occurs after connecting the array to the memory alloy, but before shipping a completed array to customers. As another example, the alteration occurs due to the connection of the memory alloy to the array. The array is altered to connect with the memory alloy. In one embodiment, the array is altered by the memory alloy after connection and prior to or during enclosing the array within a housing.

In one embodiment, the array is altered back to a desired geometry with a superelastic alloy. For example, the array is twisted, bent, warped, or shifted by handling during manufacture. The memory alloy retains the desired geometry, so deforms the array back to the desired geometry. A superelastic alloy sheet, wire, or other shape is affixed to the ultrasound array 12, such as shown in FIGS. 2-3 and 5. The superelastic alloy 16 maintains the planar or other desired geometric surface of the acoustic array 12. In some ultrasound catheter applications, the backing block of array 12, and/or other material may be thin due to size constraints. Accordingly, the dimensional stability of the transducer stack is less than otherwise could be provided. A larger number of elements may be desired, increasing a lateral (e.g., azimuth and/or elevation) extent of the array. The increased lateral extent may allow for a more easily deformed array 12. Any unwanted deformation of the array during normal manufacturing is reversed by the superelastic alloy component to the acoustic array.

The reversal is alternatively provided by a shape-memory alloy. Rather than automatically returning to the desired geometry, a temperature or other transition of the memory alloy returns or alters the array 12 to a desired geometry.

Figure 4:
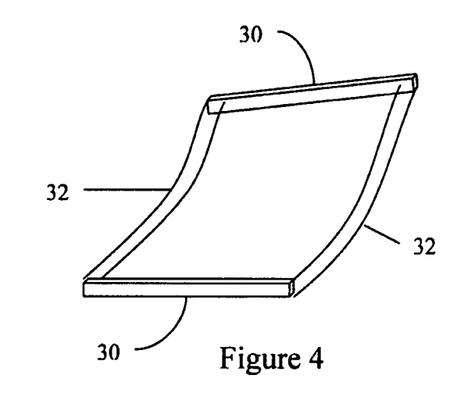
FIG. 4 is a perspective view of one embodiment of a memory alloy frame for manufacturing a transducer array.

FIG. 4 shows another use of superelastic alloy to alter the geometry of an array. A fixture includes superelastic alloy rods 32. For example, two superelastic rods 32 attach to two end pockets 30 of the same or different material. The superelastic rods 32 are bent to insert the array. 12 into the two end pockets 30. The superelastic rods 32 then unbend or bend differently due to the memory and force the array 12 to assume the desired geometry.

In one embodiment, the array 12 is altered from one shape to another shape by the memory alloy 16. The memory alloy 16 is forced to transition to a memory state different than a prior state.

Heat or other transition energy causes the alloy to alter the array geometry. For example, a shape-memory alloy, such as Nitinol, is heated. The heat is applied externally to the transducer stack and/or transducer probe. For example, heat applied to plastic weld or form a housing around the transducer stack also causes the memory alloy 16 to transition to a different geometry. Alternatively, heat may be applied internally to a transducer probe, such as by a heating element within a transducer housing and adjacent to the memory alloy 16.

Figure 7:
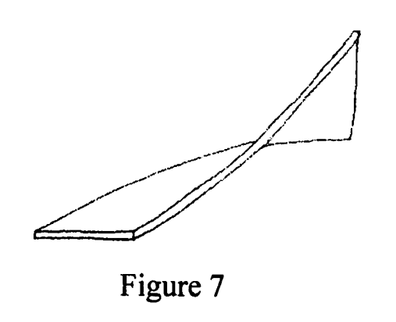

In one example alteration, the memory alloy 16 has a substantially planar shape prior to altering and alters to a curved or helical shape. FIG. 6 shows a sheet of memory alloy 16 with a substantially flat geometry (prior to bonding to the array). After transition, FIG. 7 shows the memory alloy 16 with a helical shape (after plastic welding the array within the enclosure). The elements 24 of the array 12 are twisted about a longitudinal axis of the array (i.e., the azimuth axis). The array is twisted into a helix or spiral around the longitudinal axis. The twisting provides rotation of the ends of the array, and/or rotation of elements or groups of elements of the array. For example, the array is formed as a linear array with composite elements and kerfs. The kerfs may extend into the memory alloy 16 or be formed prior to connection of the array 12 to the memory alloy 16. The transducer material, such as PZT ceramic, may be thinned to account for the added thickness of the memory alloy 16 to the highest acoustic impedance portion of the transducer stack.

The linear array is twisted by any amount. The matching layers and/or electrodes (e.g., flex circuit material) may have sufficient give or be flexible to avoid delaminating by twisting. The backing block is flexible, such as being silicone and/or epoxy with or without fillers. The backing may be other materials and/or thinned for flexibility (e.g., 0.05-0.02 inches thick).

A shape-memory alloy sheet, wire, or other shape affixed to the back of an ultrasound array 12 alters the geometry of the array 12. For example, FIG. 5 shows a shape memory rod 16 epoxy-bonded to the back of the flexible circuit conductor 14. For a subsequent catheter manufacturing, plastic welding or other heat application is performed. For example, a PET sheet with or without adhesive (PSA) is shrunk or welded around the transducer stack. As another example, a Pebax outer housing forming the catheter encloses the transducer stack by application of heat. During a plastic-welding or other heat application step, the shape-memory alloy 16 reverts to an original or memorized shape, such as the helical shape of FIG. 7. In the example of FIG. 5, the rod twists. Due to the application of heat, the thermoplastic covering 18 of the array 12 is soft enough that the array 12 can assume the geometry defined by the shape-memory alloy 16. A tip (enclosure) of a catheter may be easier to fabricate with a rectangular untwisted lumen. If the array is twisted prior to insertion, then a twisted rectangular tip lumen may be used to insert the array into the tip.

In a further embodiment, the shape-memory alloy 16 provides a frame, such as shown in FIG. 4. A combination of fixturing and stacking may be provided for further stability. For example, a sheet of Nitinol is stacked in the transducer stack. A thin wall of the sheet is bent upwards to cover a portion or entire side or sides of the transducer stack. The side walls morph differently than the stacked portion to provide a Nitinol cylinder or fixture. Thinner Nitinol may be used in the stack due to the added stability, minimizing the size of the transducer stack.

For shape memory alloy, the transformation occurs at a desired temperature. Any temperature above room and/or above likely body temperatures may be used. For example, the memory alloy 16 does not transition below 50 degrees Celsius. The stack is bound at 50 degrees Celsius or less. The transition temperature is below another manufacturing temperature, such as below the plastic welding temperature. In the case of low-durometer Pebax, the transformation occurs at a temperature below 140 degrees Centigrade. Other temperatures may be used. Separate application of heat may be used. For example, the transition does not occur during plastic welding, but occurs at another temperature applied only for transition or applied for other purposes to form the transducer probe.

Figure 8:
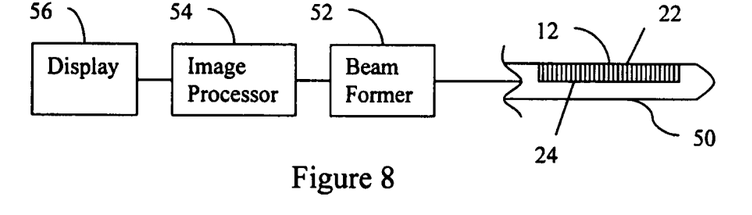
FIG. 8 is a block diagram of one embodiment of a system using an array with a memory alloy in a catheter.

In act 44, the geometry of the array 12 is fixed after the altering. The alteration sets the desired geometry during manufacture. The geometry remains the same for all subsequent use. For example, the array 12 is used in a catheter 50 as shown in FIG. 8. After fixing the geometry during manufacture, the array 12 maintains a same geometry for shipping, preparing for scanning, insertion within a patient, and/or scanning. Changes in geometry due to stress or strain may occur, but intentional changes in geometry are not provided. In alternative embodiments, the geometry of the array 12 is subsequently altered. For example, a desired shape is maintained or provided during manufacture. Structure, a hinge, other memory alloy, or other device is provided for altering the geometry during use (e.g., transitioning from a flat or a helical geometry or vise versa).

The geometry of the array 12 is held in position by a frame, housing, cured epoxy, guide wires, other structures, the memory alloy 16, or combinations thereof. For example, the memory alloy 16 alters the shape of the array 12. Material may be added to the stack and bonded with the array 12 or other material to maintain the array 12 in the desired geometry. The array 12 can then be fixed in place with an adhesive and the fixture removed. Alternatively, the fixture can be left in place, as the fixture is completely outside the acoustic path.

The memory alloy 16 remains in the stack or is removed. For example, the memory alloy 16 is on an emitting face side of the array 12. Bonding of the housing 18, bonding of the transducer stack, or added material bound to the transducer stack is added to the array 12 in the desired position. The memory alloy 16 is removed by debonding or lapping. Alternatively, the memory alloy 16 acts as a matching layer or is positioned behind the array 12.

In act 46, the array 12 is enclosed by a housing 18. The array 12 is enclosed by a protective material, such as a film of electrically insulating material. In one embodiment, the array 12 is enclosed in a transducer probe housing, such as a plastic housing for handheld use. The array 12 may be enclosed in a catheter or other housing. The enclosure is a clamshell, shrink-wrap, or other housing. For example, plastic welding encloses thermoplastic around at least a portion of the array 12. Epoxy or other bonding agent may be provided between the housing 18 and the array 12. Multiple layers of housing material may be used, such as one layer for electrical insulation and another for the outer surface of the probe.

In act 48, the array 12 is used without a change in geometry. Linear, sector, Vector® or other ultrasound scan formats may be used. In one embodiment, the array 12 has a helical geometry. The elements 24 of the array 12 are used to provide sequentially different imaging plane positions. The imaging plane from one portion of the array will face a different direction than another portion of the array. The array 12 has a fixed position, but may be altered during or for scanning.

FIG. 8 shows a system for medical ultrasound using one of the arrays manufactured according to the method of FIG. 1 or another method. The system includes the array 12 of elements 24 for medical ultrasound, a beamformer 52, an image processor 54, and a display 56. Additional, different, or fewer components may be provided. For example, the system includes the array 12 without the beamformer 52, image processor 54, and/or display 56. These imaging electronics may be in a separate ultrasound imaging system. The transducer releasably connects with the imaging system.

The array 12 is used in a transducer probe, such as a medical ultrasound transducer. The transducer probe is used outside of a patient, such as a handheld transducer probe. Alternatively, the transducer is used within a patient, such as a catheter 50, a transesophegeal, vaginal, intercavity, intraoperative, or other probe. The array 12 is connected with or positioned in the transducer probe. A window or lens is over the array 12 for acoustic scanning from an emitting face 22 of the array 12 from within the probe.

The array 12 has a plurality of elements 24, backing block, electrodes, and a matching layer. Additional, different, or fewer components may be provided. For example, two or more matching layers are used. The backing block material absorbs acoustic energy to limit or prevent reflections received from the back of the array 12. The matching layers provide a more gradual transition between acoustic impedance, minimizing reflection from the boundary between the transducer and the patient. The electrodes interact with the elements to transduce between acoustic and electrical energy. The variation of potential or distance between electrodes across an element causes electrical signal generation or acoustic energy, respectively.

In one embodiment, flex circuit resides between the backing block and the PZT. The flex circuit bends around the side of the backing block and is folded (in an accordion fashion) behind backing block. Within the flex connection bundle (accordion) 14, the flex circuit is connected to the bundle of conductors that transmit the signals between the beamformer 52 and the array 12. In one variation, the flex connection bundle 14 resides between the backing block and the alloy 16 (see FIG. 2). In another variation, the alloy 16 is positioned between the backing block and the flex connection bundle 14 (see FIG. 3).

The elements 24 contain piezoelectric material. Solid or composite piezoelectric materials may be used. Each element is a rectangular solid, cubic, or six sided, but other surfaces may be provided. For example, the emitting face 22 of one or more elements 24 is concave or convex for elevation focusing or frequency based directivity. Alternatively, a microelectromechanical device, such as a flexible membrane, is used. Any now known or later developed ultrasound transducer may be used. Longer elements in elevation as compared to wavelength may provide increased elevation directivity.

Any number of elements 24 may be provided, such as 64 elements. 128 or other number of elements 24 may allow for more or larger apertures. The elements 24 are adjacent to each other, such as having substantially wavelength or less spacing between the centers of adjacent elements 24. For example, the elements 24 have half wavelength spacing with kerfs acoustically separating each element 24. The wavelength spacing is based on a center, average, imaging, or other frequency of operation of the array 12. Sparse arrays 12 with greater spacing between elements 24 may be used.

The elements 24 are positioned along an azimuth axis. For a one-dimensional array 12, the elements 24 are in a single row along the azimuth axis. Thirty-two, fifty or more, sixty-four, one hundred and twenty eight or other numbers of elements 24 may be used. The array 12 may be linear or curved linear. A curved linear array 12 has ends or a middle that extend towards or away from the azimuth axis, but the elements 24 are still positioned along the azimuth dimension. Due to the curve, some elements 24 of the array 12 are at different depths or ranges.

Multi-dimensional arrays 12 may be used. For example, two or more rows of elements 24 are adjacent to each other along the elevation dimension. 1.25, 1.5, 1.75 or 2D arrays may be provided. The spacing between elements 24 along the elevation dimension is the same or different than along the azimuth dimension, such as a 2×64 array with half wavelength spacing between all adjacent elements in azimuth. The elements are long in elevation, such as having a 3-20 wavelength elevation width, but may be half wavelength or have other spacing.

The side of the elements 24 covered by the matching layer, closer to the region to be scanned, and/or opposite the backing block is the emitting face 22. Acoustic energy is transmitted from and received at the emitting face 22 of the array 12. The angle of acoustic energy relative to the emitting face 22 affects the sensitivity of the elements 24 to the energy. The elements 24 are more sensitive to the energy at normal incidence to the elements 24.

In one embodiment, some of the elements 24 of the array 12 are rotated. The rotation is about the azimuth axis. The azimuth axis extends through the elements 24, the backing, the emitting face 22, or adjacent to the array 12. The rotation forms a helical or spiral pattern of the elements 24. The adjacent elements 24 are arranged in a helix along the azimuth axis. One element 24 is rotated by a different amount about the axis than other elements 24. The angle of greatest sensitivity is different for the rotated element 24 as compared to for another element 24. The rotation about the azimuth axis may be in addition to rotation away from the axis, such as associated with a curved array.

Each element 24 is rotated by a different amount. For example, the elements 24 at opposite ends of the array 12 are rotated about the azimuth axis by at least 10, at least 15 or other greater or lesser number of degrees relative to each other. The azimuth centerline is straight or may rotate or twist. Greater or lesser total rotation may be used. Each of the elements 24 in between are rotated a different amount to step the rotation between the ends. For example, each element 24 rotates about 0.47 degrees as compared to an adjacent element 24 (e.g., 64 elements 24 with 30 degrees total rotation provide 0.47 degrees per element 24). Alternatively, groups of elements 24 are rotated a same amount relative to another element 24 or group of elements 24. For example, half the array 12 is rotated one amount and the other half another amount. Any number of steps may be used, with symmetrical or asymmetrical groupings of elements 24. For example, a center group of elements 24, periodic group of elements 24 or other arrangement of elements 24 face a same direction, but other elements are rotated. In one embodiment, a center half of the elements 24 (e.g., center 64 elements 24) are straight or have a same rotational orientation about the azimuth axis, but one quarter of the elements 24 on each end (e.g., 32 elements 24 on one end and 32 elements 24 on the other end) are rotated in a spiral. The rotation is a single step or a plurality of steps.

In general, a larger aperture in elevation provides increased elevation directivity and narrower elevation beamwidth. By twisting the array in elevation, a sub-aperture of elements is used in concert to form an image plane. The total number of independent beams that can be formed by an array is on the order of the number of elements of an aperture. By varying the total twist relative to the elements angular beamwidth, there is a tradeoff between resolution in azimuth and the elevation angular width of the volume formed.

During manufacture, after manufacture, during use and/or combinations thereof, the transducer includes memory alloy 16. The memory alloy 16 connects with the array 12. For example, the memory alloy 16 establishes, during manufacture, a fixed geometry of the array. The memory alloy 16 establishes the fixed geometry such that the fixed geometry does not change after the manufacture. The memory alloy 16 assists in holding an array 12 in a position for manufacture and/or in altering the position to provide a desired geometry. For example, the memory alloy 16 is flat for ease of assembly of the transducer stack, but transitions to a helical pattern during manufacture for use of the array 12 in a helical pattern.

Any now known or later developed memory alloy may be used. For example, a shape-memory alloy is used, such as Nitinol. The shape-memory alloy has a current shape and a remembered shape. Upon application of energy, such as heat, the shape-memory alloy returns from the current shape to the remembered shape. The transition alters the emitting face 22 of the array 12. For example, the emitting face 22 is altered from a substantially planar geometry to a fixed, non-planar geometry.

Another example memory alloy 16 is a superelastic alloy. Superelastic alloys may be bent, twisted or otherwise altered, but return to a remembered shape or geometry. For example, the superelastic alloy returns the emitting face 22 of the array 12 to a desired geometry after any distortion. The desired geometry may be fixed at the conclusion of manufacturing.

The memory alloy 16 may be connected in any manner with the array 12 to provide the desired influence. For example, the memory alloy 16 is stacked with the array 12 along a range dimension as shown in FIGS. 2-3 and 5. The range dimension is substantially orthogonal to the emitting face 22 at a given location. The sheet of memory alloy 16 has a substantially same azimuth and elevation extent as the array 12, but may be smaller or larger. As another example, the memory alloy 16 is part of a frame, such as shown in FIG. 4.

The elements 24 are held in place or altered to return to a desired geometry by the memory alloy 16. During manufacture, additional material may be added to hold the elements 24 at a geometry established by the memory alloy 16. The additional material, the memory alloy 16, or both fix the position, such as permanently, for later use. For example, the enclosure 18 (e.g., Pebax) is premolded to be a close fit between the array 12 and flex connection bundle 14. When the enclosure 18 is melted, the array 12 is twisted by the alloy and all open spaces are filled with material from the enclosure 18 or epoxy added within the enclosure 18. Upon curing, the elements 24 are held in position. As another example, a frame holds the elements 24 in place. In another example, epoxy or other bonding agent cures against a portion or the entire array 12 to hold the array 12 in position. Other materials and associated structures may be used. For the catheter embodiment, the body of the catheter 50 may twist or rotate to avoid interference with, hold in place, or assist in holding in place the rotated elements 24.

The backing block material, electrodes, ground plane, and/or matching layers are deformable, allowing twisting with the elements 24. For example, an array 12 normally used as a linear array may be twisted without further changes in manufacture processes. Alternatively, one or more of these layers are formed after alteration to avoid deformation.

Referring to FIG. 8, electrical conductors connect the elements 24 of the array 12 to the receive beamformer 52. The conductors are cables, coaxial cables, traces, wires, flex circuits, wire jumpers, combinations thereof, or other now known or later developed conductor. One conductor is provided for each element 24. Alternatively, fewer conductor than elements 24 may be used, such as for switched apertures, partial beamforming, or multiplexing. The conductors are separately addressable as a single array 12. Each element 24 may be selectively used for a given aperture and associated electronic steering. Alternatively, some elements 24 are useable with only a subset of possible apertures.

The array 12 is positioned within the catheter 50. The array 12 may fit within a 10 French, 3.33 mm, or other diameter catheter 50. The conductors are routed through the catheter 50 to the beamformer 52. The catheter transducer is used for imaging. The images assist in diagnosis, catheter or tool guidance, and/or therapy placement. The geometry established by the memory alloy 16 may assist in imaging. For example, maintenance of the array 12 as flat or curved with the catheter 50 may reduce imaging artifacts and/or allow sector scanning. As another example, the memory alloy 16 alters the array 12 into a helical pattern. By including the helical array 12 within the catheter 50, three-dimensional scanning and image representations may be used. Alternatively, the rotated elements 24 of the array 12 are used in other transducers.

The beamformer 52 includes a plurality of channels for generating transmit waveforms and/or receiving signals. Relative delays and/or apodization focus the transmit waveforms or received signals for forming beams. The beamformer 52 connects with the conductors. The beamformer 52 selects an aperture including one, some, or all of the elements 24 of the array 12. Different apertures may be used at different times. The aperture is formed by using the elements 24 for transmit and/or receive operations while not using other elements. The beamformer 52 is operable to scan from a plurality of apertures formed by adjacent groups of the elements 24. The apertures may walk through regular increments or skip to different portions of the array 12.

For scanning, the beamformer 52 electronically focuses along the azimuth direction. A plurality of scan lines using an aperture is scanned. During receive operations, the focus may vary as a function of depth. An elevation focus is provided by a lens and/or element sensitivity, or the array 12 is not focused in elevation. In alternative embodiments, the beamformer 52 connects with elevation spaced elements for at least partial electric focusing and/or steering in the elevation dimension.

In the helical geometry embodiment, different planes are scanned by scanning from different apertures of the array 12. The rotation of the elements 24 positions the scan planes for different apertures at different amounts of rotation about the azimuth axis. Short sections of the array 12, on average, point in different directions offset from sections of the array 12 on either side. For example, the first eight elements 24 of an aperture formed on an array 12 with a total rotation of 32 degrees over sixty four elements 24 rotated by sixty four steps have an angle of −14 degrees. The non-coplanar scan planes of the sequence of eight sequential apertures of eight elements each are at angles of −10, −6, −2, +2, +6, +10 and +14. These eight apertures define eight diverging planes spaced apart in elevation. The diverging planes are stacked adjacent to each other to scan the volume. Using different apertures with some or all elements 24 not in common allows for scanning different planes or regions.

The size of each aperture may be limited by the amount of twist. The useable directivity of the elements 24 within an aperture should overlap, such as overlapping the elevation directivity of the elements 24 at the ends of each aperture. Elevation spaced elements, such as two rows of elements, may allow less twist with electronic assisted steering in elevation to reduce beam spreading and allow longer apertures.

The image processor 54 is a detector, filter, processor, application specific integrated circuit, field programmable gate array, digital signal processor, control processor, scan converter, three-dimensional image processor, graphics processing unit, analog circuit, digital circuit, or combinations thereof. The image processor 54 receives beamformed data and generates images on the display 56. The images are associated with a two-dimensional scan.

Alternatively or additionally, the images are three-dimensional representations. Data representing a volume is acquired by scanning. The processor 54 generates a three-dimensional data set as a function of the scanning by the beamformer. The data of the three-dimensional data set may be interpolated to a Cartesian grid or maintained in a scan format. The relative position of the planes used for scanning may be known or assumed based on the aperture position and rotation of the corresponding elements 24. Any rendering may be used, such as projection, volume, and/or surface rendering. The processor 54 generates the three-dimensional representation from the data representing the volume.

A volume scan may be obtained with the array 12 having a helical geometry. By using the twist of the emitting face 22 of the array 12, different planes within a volume may be scanned. The planes are spaced apart in the elevation dimension, such as extending at different amounts of rotation from the array 12. By electric steering in azimuth, the scans may cover a similar region or have similar extents in the azimuth-range dimension. Alternatively, the array 12 is curved or flat without twist. A volume may be scanned by movement of the array 12 and/or the catheter 12. In other embodiments, a multidimensional array 12 or an array with concave or convex elements allows electronic or frequency steering, respectively, to scan a volume.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A transducer for medical ultrasound, the transducer comprising:
    a plurality of elements defining an emitting face of an array, the elements spaced at least along an azimuth axis; and
    a memory alloy connected with the array, the memory alloy being stacked with the array along a range dimension, the range dimension being orthogonal to the emitting face;
    wherein the memory alloy establishes, during manufacture, a fixed geometry of the array, the fixed geometry maintained without change after manufacture and during use of the transducer.

2. The transducer of claim 1 wherein the elements are rotated about the azimuth axis in a helical pattern, wherein the emitting face is twisted based on the rotation, and wherein a memory position of the memory alloy corresponds to the helical pattern.

3. The transducer of claim 1 wherein the memory alloy comprises a shape-memory alloy.

4. The transducer of claim 1 wherein the memory alloy comprises a superelastic alloy.

5. The transducer of claim 1 wherein the plurality of elements includes at least fifty elements along the azimuth axis, each of the elements rotated relative to at least one adjacent element.

6. The transducer of claim 1 wherein the memory alloy comprises a sheet of memory alloy having a same azimuth and elevation extent as the array.

7. The transducer of claim 1 further comprising:
    a catheter;
    wherein the array is positioned within the catheter.

8. A transducer for medical ultrasound, the transducer comprising:
    a plurality of elements defining an emitting face of an array, the elements spaced at least along an azimuth axis; and
    a memory alloy connected with the array, the memory alloy operable to establish, during manufacture, a fixed geometry of the array;
    wherein the memory alloy is operable to establish the fixed geometry such that the fixed geometry does not change after the manufacture.

9. The transducer of claim 8 wherein the memory alloy comprises a superelastic alloy operable to return the emitting face of the array to the fixed geometry after any distortion.

10. The transducer of claim 8 wherein the memory alloy comprises a shape memory metal operable to alter the emitting face from a planar geometry to the fixed geometry, the fixed geometry being non-planar.

11. The transducer of claim 10 wherein the shape memory metal has a transition temperature above a bonding temperature and below a plastic welding temperature.

12. The transducer of claim 8 wherein the memory alloy is stacked with the array and extends along at least one side of the stack.

* * * * *